United States Patent [19]

Dukhan et al.

[11] Patent Number: 4,750,474
[45] Date of Patent: Jun. 14, 1988

[54] INCUBATOR

[76] Inventors: Saul Dukhan, 1 Bar Kochba Street, Dimona; Amos Sadan, 17 Arthur Ruppin Street, Beer Sheva; Zeev Avnet, 12 Hogla Street, Beer Sheva; Itshak Zagha, 74 Vingate Street, Beer Sheva; Shlomo Greenberg, 5 Yasmin Street, Beer Sheva, all of Israel

[21] Appl. No.: 863,945

[22] Filed: May 16, 1986

[30] Foreign Application Priority Data

May 16, 1985 [IL] Israel ............................. 75215

[51] Int. Cl.4 .................................. A61G 11/00
[52] U.S. Cl. ..................... 128/1 B; 128/205.26
[58] Field of Search ............. 128/1 B, 30, 205.26, 128/202.26; 312/209, 236, 293, 6, 173, 239, 252, 257, 283–289, 309, 322

[56] References Cited

U.S. PATENT DOCUMENTS

| D. 189,870 | 2/1972 | Brush | 128/1 B |
|---|---|---|---|
| 2,292,120 | 8/1942 | Hanby | 128/1 B |
| 2,822,803 | 2/1958 | Huxley et al. | 128/30 |
| 3,070,086 | 12/1962 | Smith et al. | 128/1 B |
| 3,158,150 | 11/1964 | Croasdaile | 128/1 B |
| 3,490,443 | 1/1970 | Decupper | 128/1 B |
| 3,529,590 | 9/1970 | Grosholz | 128/1 B |
| 3,858,570 | 1/1975 | Beld et al. | 128/1 B |
| 3,877,437 | 4/1975 | Maitan et al. | 128/1 B |
| 4,167,298 | 9/1979 | Plattner | 312/284 |
| 4,191,174 | 3/1980 | Martin | 128/1 B |
| 4,321,913 | 3/1982 | Maluta et al. | 128/1 B |
| 4,492,279 | 1/1985 | Speckhart | 128/1 B |
| 4,509,570 | 4/1985 | Mercey et al. | 128/1 B |

Primary Examiner—Edward M. Coven
Assistant Examiner—K. M. Reichle
Attorney, Agent, or Firm—Fleit, Jacobson, Cohn & Price

[57] ABSTRACT

The invention relates to an incubator for babies. It is of special value for the treatment of premature infants as an intensive care unit. A cradle is surrounded by a housing with two movable curved panes, with a curtain of pretreated air. Advantageously the incubator includes artificial illumination and IR-radiation heating. The incubator is provided with convenient access and various accessories required for an intensive care unit.

5 Claims, 7 Drawing Sheets

ć# INCUBATOR

FIELD OF THE INVENTION

The invention relates to a versatile static incubator for premature infants which can be used both as a standard type incubator and also as an intensive care incubator. Means are provided for maintaining a predetermined temperature, for maintaining a predetermined humidity and for the weighing of the infant without removal from the incubator. There exists a variety of modes of access to the interior, and it is possible for more than one person to have simultaneous access to the interior of the incubator, while an air curtain maintains the desired conditions in the interior of the incubator. The incubator advantageously includes a control system and means for providing a continuous indication of the conditions in the interior of the incubator, and for providing an alarm if any undesired change of these conditions has taken place.

BACKGROUND OF THE INVENTION

There exists a great variety of incubators for prematurely born infants. These provide a controlled temperature and humidity inside the incubator, simulating the optimum conditions required by the infant. Generally means are provided for providing good visibility of the interior, and means are also provided for an easy access to the interior. Conventional incubators are generally divided into two basic types:

a. conventional incubators for prematurely born infants which are healthy;

b. incubators of the intensive care type intended for problematic cases of ill infants, which are generally provided with IR-radiation heating means.

Various means of heating are resorted to such as the circulation of heated humidified air, or the use of radiant heat. It is one of the main problems to maintain a uniform temperature in the interior, and not to disturb this drastically when the incubator is opened to provide access to its interior by a physician or nurse, applying some treatment to the infant.

The need to have two distinct types of incubators, and the problem of providing an essentially constant temperature and degree of humidity in the interior of the incubator are overcome to a large extent by the novel design of the incubator of the present invention, which provides some novel features of great practical utility.

SUMMARY OF THE INVENTION

There is provided an improved incubator for premature infants which can be used as a standard incubator and also as an intensive care incubator. The incubator comprises a transparent upper section, two wings of which are in the form of cylindrical segments of equal radius, which are rotatable about a common axis; there is also provided a "roof-section", which is generally static, but which can be removed when the unit is to be used as an intensive care unit.

The two cylindrical segments making up the two windows are double-walled, each wall made of a transparent plastic material, providing for good visibility and for efficient thermal insulation. A counterweight is provided for each such segment-section, which makes it possible to maintain such member in any desired position.

The weighing of a premature infant is of great importance, and hitherto the infant had to be removed from the incubator for this purpose.

In the incubator of the invention a scale is provided so as to provide for the weighing of the infant whenever desired without removal of the infant from the incubator.

Heating is provided by means of a flow of preheated air between double walls of its lower half, which air is also given the required degree of humidity. The air flows upwards and establishes an air-curtain, which maintains an essentially constant temperature even when a window is opened.

There is further provided an opening at the upper side of the incubator, providing access to the head of the infant, or for the partial removal of the infant in this direction.

To summarize the characteristics of the novel incubator, which can be used as a standard incubator and as an intensive care unit, the main ones are as follows:

a. an isolated atmosphere of predetermined temperature and humidity is provided;

b. the temperature is essentially uniform throughout the interior of the incubator;

c. there is provided good visibility of the interior;

d. easy access is provided, if required, for more than one person;

e. the construction provides for a low noise level inside the incubator;

f. there is provided a scale within the interior of the incubator making it possible to weigh the infant without removal from the incubator;

g. there is advantageously provided a control system for maintaining temperature and humidity at a predetermined level, and indicating means for the essential parameters. There are also advantageously provided automatic alarm means for sounding an alarm when a certain parameter of the environmental conditions in the incubator is exceeded.

h. When used as an intensive care unit, radiant heating means are provided from above (an IR-heater).

The upper part consists essentially of three sections:

(i) The upper roof section which can be removed when the unit is to be used as an intensive care unit with IR-heating from above;

(ii) two mobile sections in the shape of segments of a cylinder, of equal radius, which are double-walled, and which each span a predetermined segment of the cylindrical upper half of the incubator. These are advantageously provided with counterweights for keeping them in any desired open, closed or partially open condition. The air circulation system comprises a heater and fan; the air is humidified to the desired degree of humidity. The air is introduced at the lower part of the cradle, and flows upwards along the inner wall of the double-walled segments, the interior of which is thus heated. The air flowing upwards forms an air-curtain and heats the interior of the incubator to an essentially uniform temperature.

There is advantageously provided a weighing scale at the base of the cradle, permitting weighing of the infant without removal and without disconnection from medical instrumentation.

There are also advantageously provided means for measuring and indicating air and skin temperature, and also an automatic alarm system.

When conditions make it necessary to operate in the intensive care mode, the roof-section is removed; the two cylindrical upper wall-sections are slid underneath the cradle section, and the heating is changed over to IR-heating from above.

The degree of heating thus applied is controlled by the skin measurement means and by other sensors.

It is possible to operate the incubator with both cylindrical-segment sections open, with the air-current of circulating air, and if required, with additional IR-heating from above.

The interior of the incubator can be easily cleaned and decontaminated.

The novel incubator system is described in the following.

It is to be clearly understood that this is by way of illustration only and that modifications and changes in the construction and nature of components may be resorted to without departing from the scope and spirit of the present invention.

DESCRIPTION OF THE PREFERRED EMBODIMENT

As stated above, the following detailed description describes by way of illustration a specific embodiment, this being in conjunction with the enclosed schematical drawings, which are not according to scale and in which:

As illustrated in the Figures, where identical parts are given the same numbers, an incubator according to the invention is mounted on a support structure 11, which comprises a base 12, advantageously provided with wheels 13. The support comprises two support columns, a lower one 14, and a higher one 14'. Through these there pass conduits of fluids and cables from the control unit cabinet 15. The cradle 17 has a bottom portion 33 and is pivotably connected to both columns 14 and 14'. To column 14' there is connected at its top, a unit 18 which houses lamps for illumination, IR-radiation sources and lamps for phototherapy. There is provided a circumferential rim 19, also attached to the columns 14 and 14', which provides for ease of handling. The incubator comprises two side-wall structures 21 and 22, provided with rim sections 23 and 24, respectively. The upper part of these rim sections supports the essentially rectangular, slightly curved roof section 25, which is present when the incubator is used as a conventional one, but which is removed when it is used as an intensive care unit.

There are provided two wing-shaped double-walled transparent windows 26 and 27, each of which consists of two curved panes of a transparent plastic, which provide for good visibility. The radius of the windows 26 and 27 is such that they can be moved all around the cradle structure, i.e. by 360°, if one window is simultaneously displaced with the other window to thereby provide a free path of travel. Each of the said windows comprises two sections of different radius, which define a segment of a cylinder, thus window 26 comprises bent sheets 26' and 26", and window 27 bent sheets 27' 27", between which there is provided an insulating air space 26'''' and 27''', respectively, there being provided frame members 28 and 29, respectively, which seal these window structures in a hermetic manner. Also, the upper roof section 25 is a double-walled one, with an air-space between two panes, providing for temperature insulation, as is shown in greater detail in FIG. 2. The two windows 26 and 27 are each provided with a counterweight, as shown in detail, and also with a friction mechanism, which holds the windows in any angular position to which such window is moved.

Figure 7:
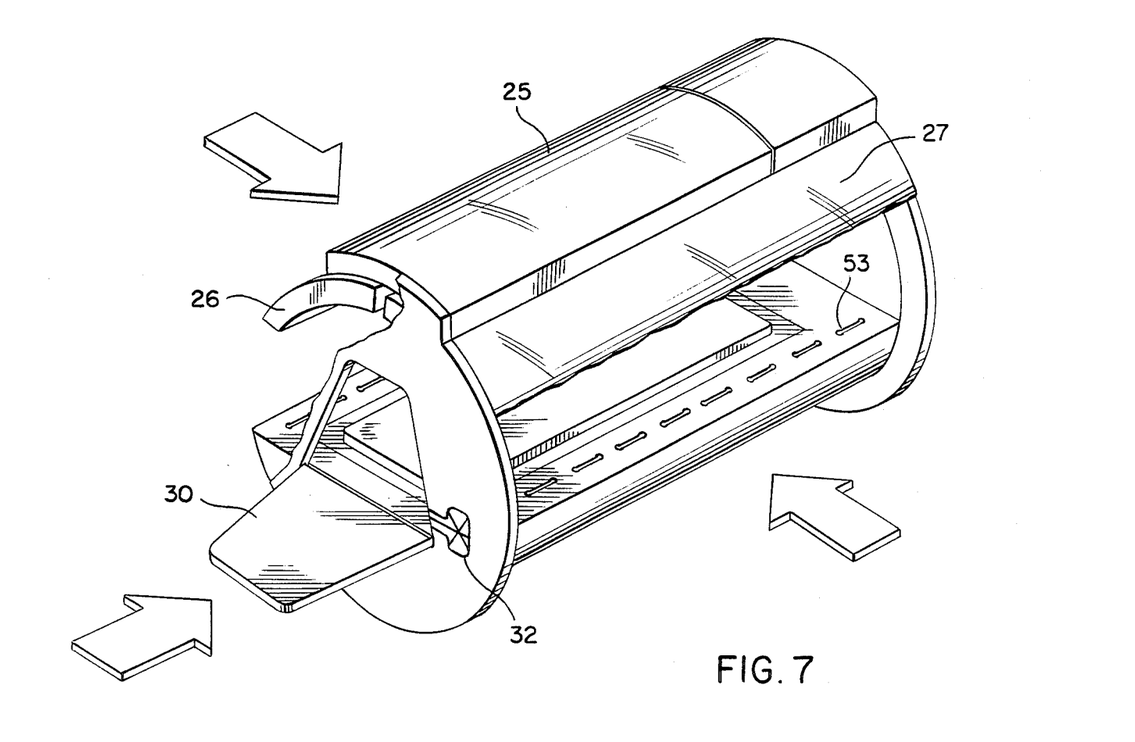
FIG. 7 is a perspective view of the cradle of the incubator indicating the access to the interior of the incubator.

In the side-wall 21, there is provided a hinged trapeze-shaped closure member 30, which can be opened to the position shown in FIG. 7, thus making it possible to pull out the mattress of the cradle with the infant positioned on same, providing easy access for any treatment of the head or other upper body section.

Figure 6A:
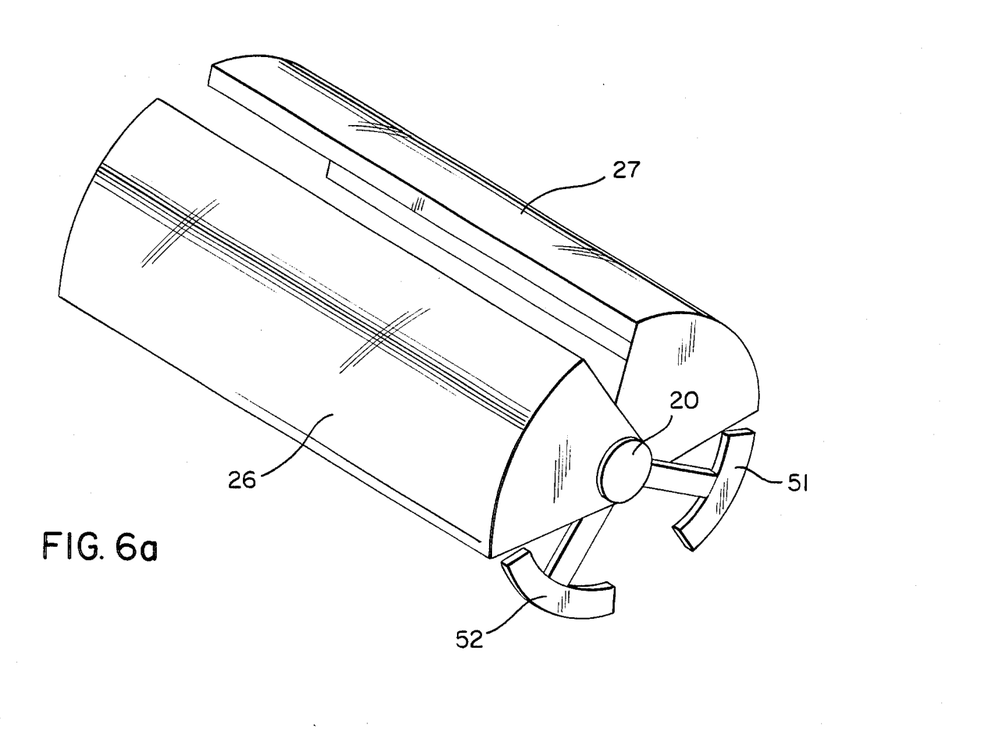
FIG. 6a illustrates the lateral windows (cylindrical segments) with their counterweights in a perspective view.

In the side-wall 21 there are also provided resealable openings 31 and 32, contacting closure member 30, through which there can be passed into the interior of the incubator conduits of liquids or gases, probes or any other connections to the outside. As set out above, the window structures 26 and 27 can be kept shut, or these can be moved to any position around the incubator, providing for any desired opening, as illustrated for example in FIG. 3, 6a, 6b and and 7. As shown, they can be lowered to a position (FIG. 4) where they are located around the bottom section of the cradle section of the incubator.

The air is filtered, it passes through inlet port 34, mixed with re-circulated air coming via a conduit to inlet 35, moved by means of blower 36, through a heater 36', water pool 36" for controlled humidification and via pipe 37 to the inner space of the incubator 45. The air moves upwards as indicated by the arrows 40, 41, 43 and 44, thus establishing an air-curtain which persists even when the side-windows are opened. The circulating air heats the windows 26 and 27, and establishes a predetermined temperature and humidity in the interior of the incubator. Part of the air is recirculated via a conduit to intake 35.

Figure 1:
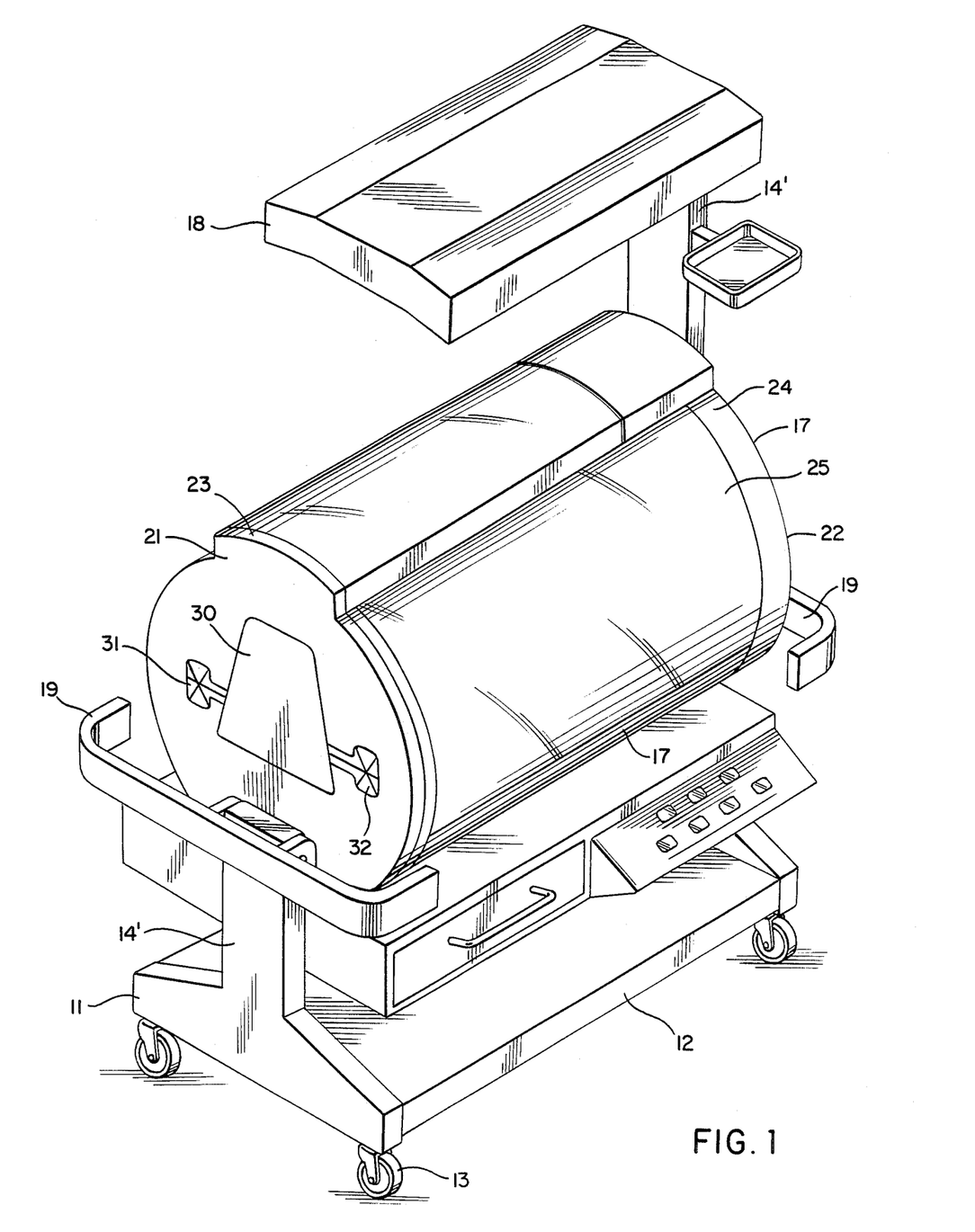
FIG. 1 is a perspective view of an incubator.
Figure 2:
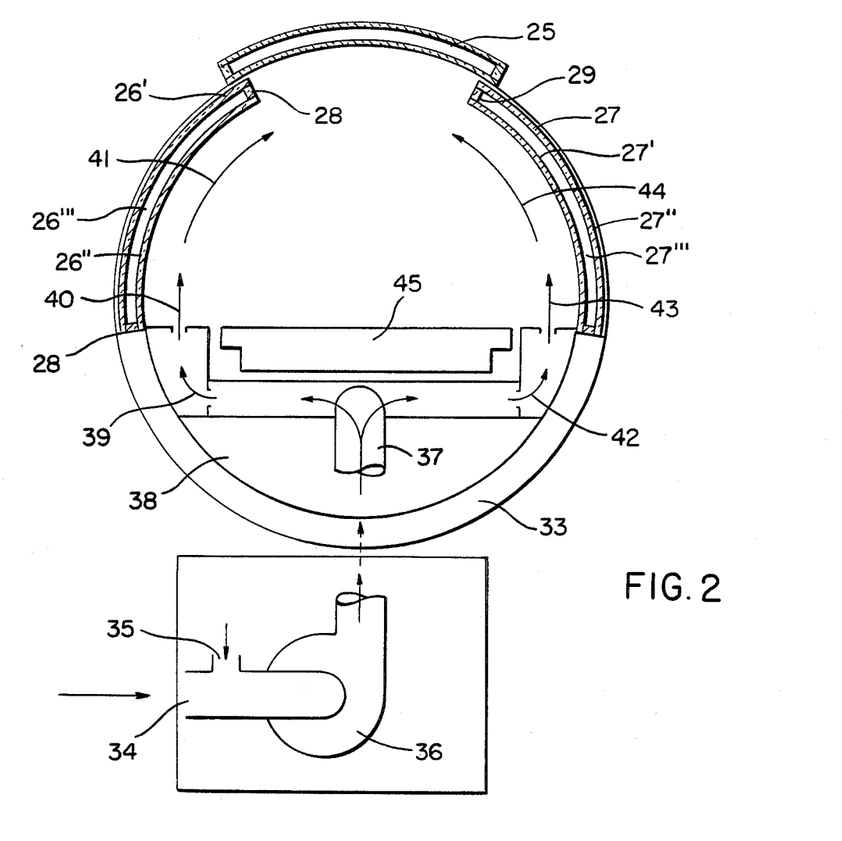
FIG. 2 is a schematic sideview, in partial section, indicating air flow in the standard mode of operation.
Figure 3:
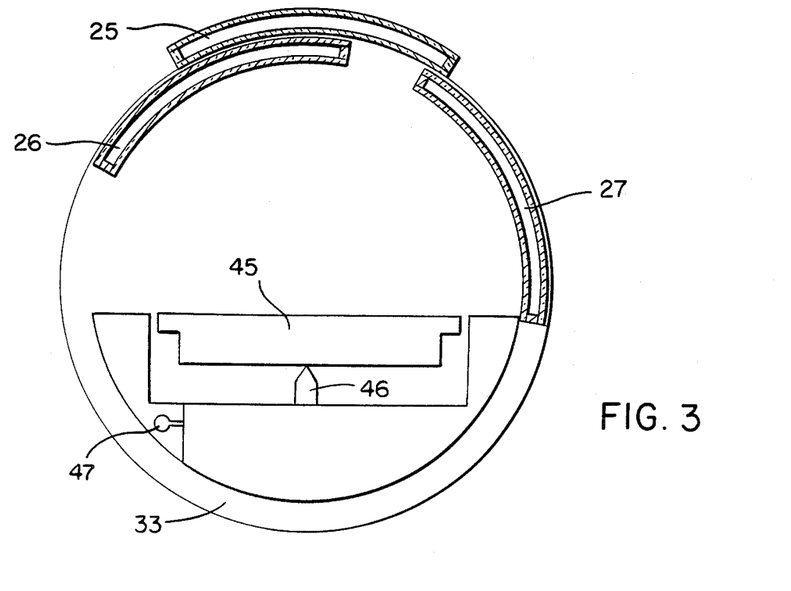
FIG. 3 is a side-view about the center of the incubator, in partial section, with one window partially open, illustrating the weighing means.
Figure 5:
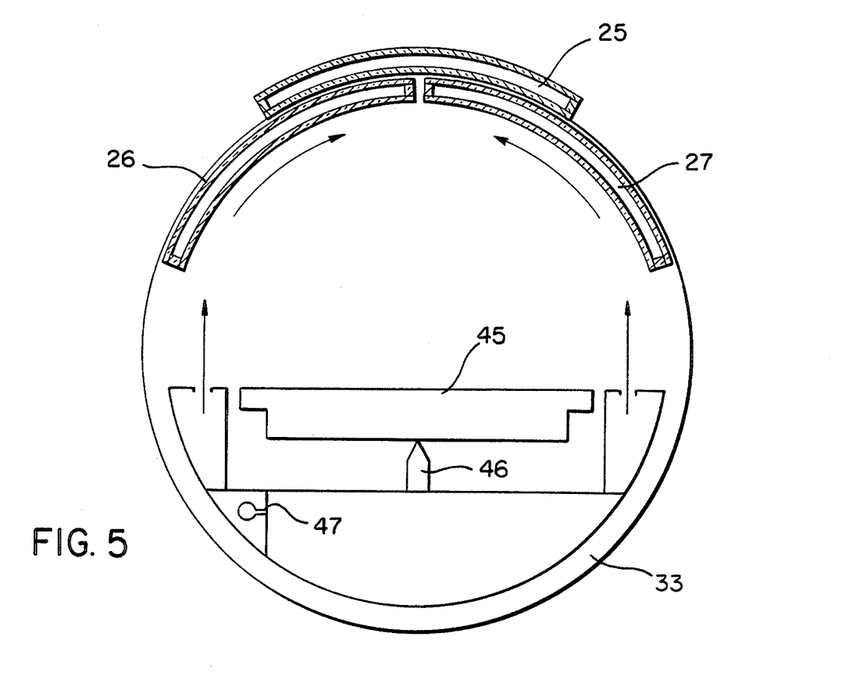
FIG. 5 is a sectional side-view with two open side windows, illustrating the air curtain.

As shown in FIG. 3, the left-hand window 26 can be lifted to any intermediate position, between completely closed (as shown in FIG. 2) up to the position shown in FIG. 5, and practically around the cradle hollow to bottom portion 33. It can be lowered into the lower part of the incubator. In the incubator space there is provided the cradle and the mattress 45. As shown in FIG. 3, this is supported by the load cell 46, which is connected to measuring means, thus providing a scale on which the infant can be weighed while in the incubator, without removal to the outside. As both wide windows can be opened, there is provided convenient access to the interior for more than one person of the hospital personnel. The bed and mattress can be tilted by an angle of inclination by pulling out the tilt-handle 47.

Figure 4:
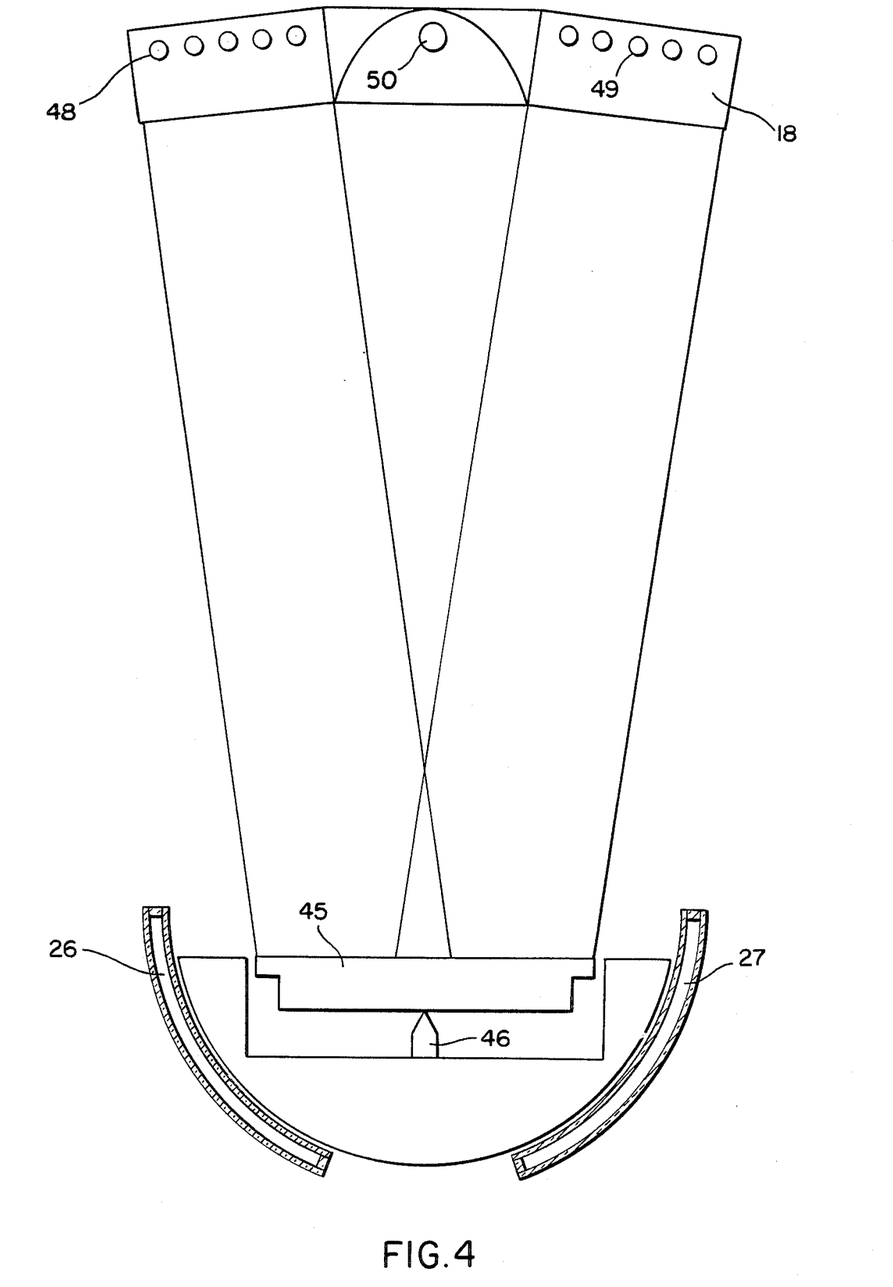
FIG. 4 illustrates the intensive-care mode of operation.

The incubator can be used both as a normal incubator, and also as an intensive care unit. For use as an intensive care unit, the incubator is used as shown in FIG. 4; both the side-windows 26 and 27 are slid around the lower part of the cradle, and upper section 25 is removed, and the illumination/IR unit 18 is activated: this comprises radiant heaters 48 and 49 and illumination means which includes a light source 50. The two transparent side-walls which define sections of a cylinder, are provided with balancing and stabilizing means illustrated in FIGS. 6a and 6b, the left-hand window 26 is provided with a counterweight 51 while right-hand window 27 is provided with a counterweight 52. These permit the positioning of the windows at any position desired, where they will remain as the weight is balanced by the respective counterweight. There are also provided friction-retaining means for stopping the window at any position.

Figure 6B:
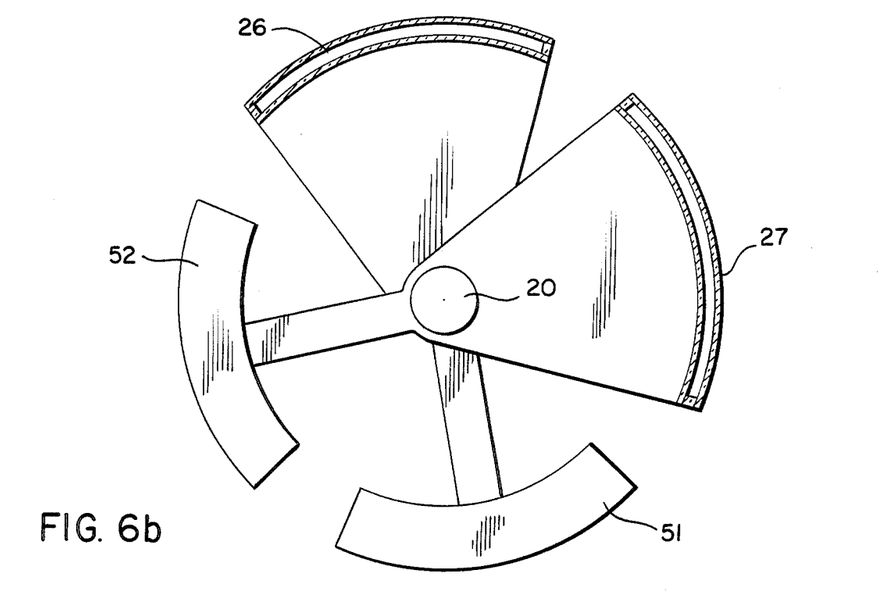
FIG. 6b is a cross-sectional view of FIG. 6.

In FIG. 5 the windows are shown with the lateral covers in place; FIG. 6b illustrates the windows with details of the double-walled windows. This system permits easy access to the interior of the incubator and providing openings at any desired angle. The access to the interior of the cradle is illustrated in FIG. 7, with partially opened side-windows 26 and 27, with open trapeze-shaped opening section 30. The slits 53 indicate openings for the air entering the interior of the incubator.

Even when the incubator is in a position as shown with windows 26 and 27 in a quite open position, the air-screen minimizes heat losses and the interior of the incubator is maintained at essentially the same temperature and humidity.

Figure 8:
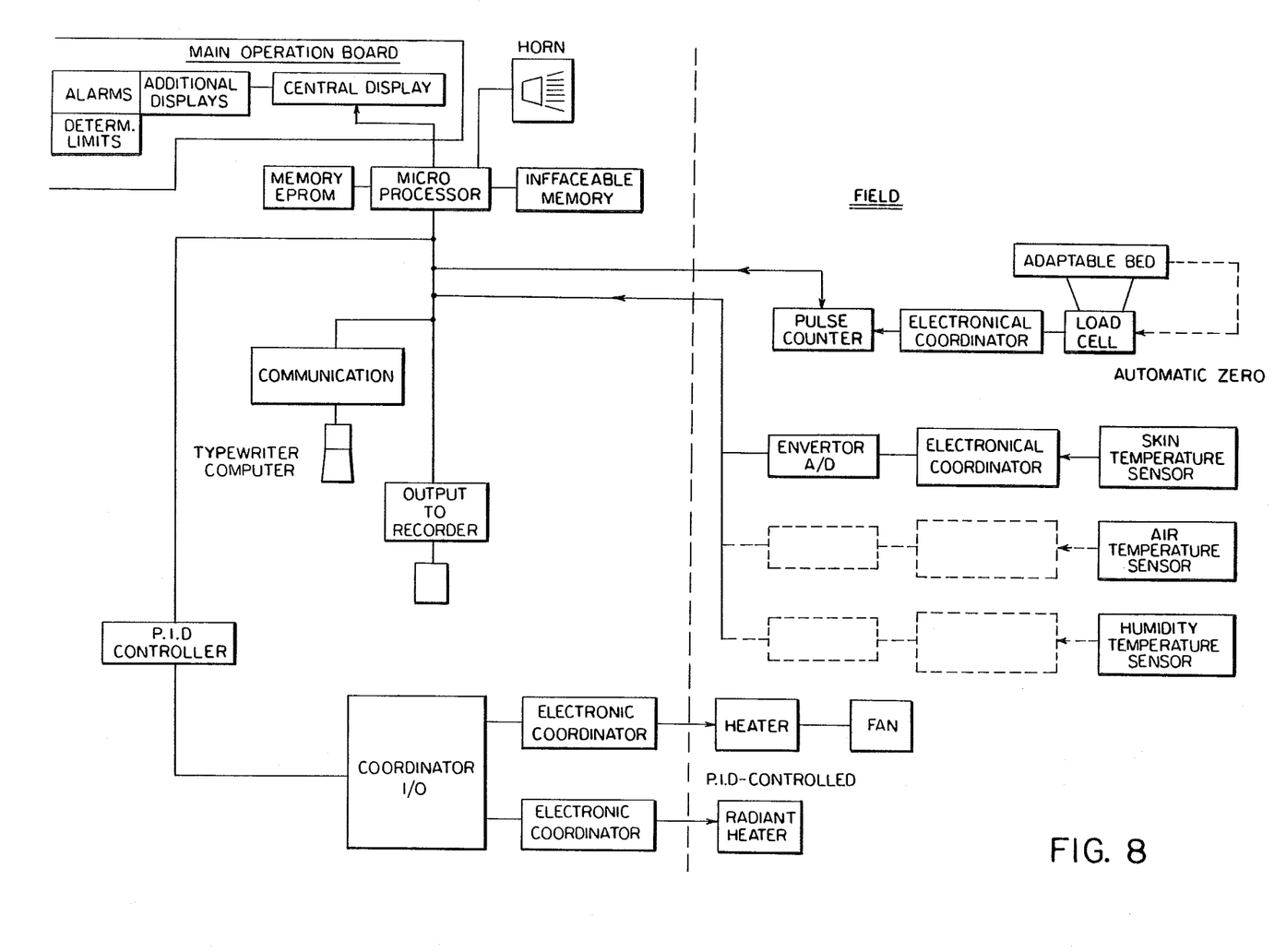
FIG. 8 is a perspective view illustrating air flow in the standard mode of operation with air humidification, heating and circulation means.
Figure 9:
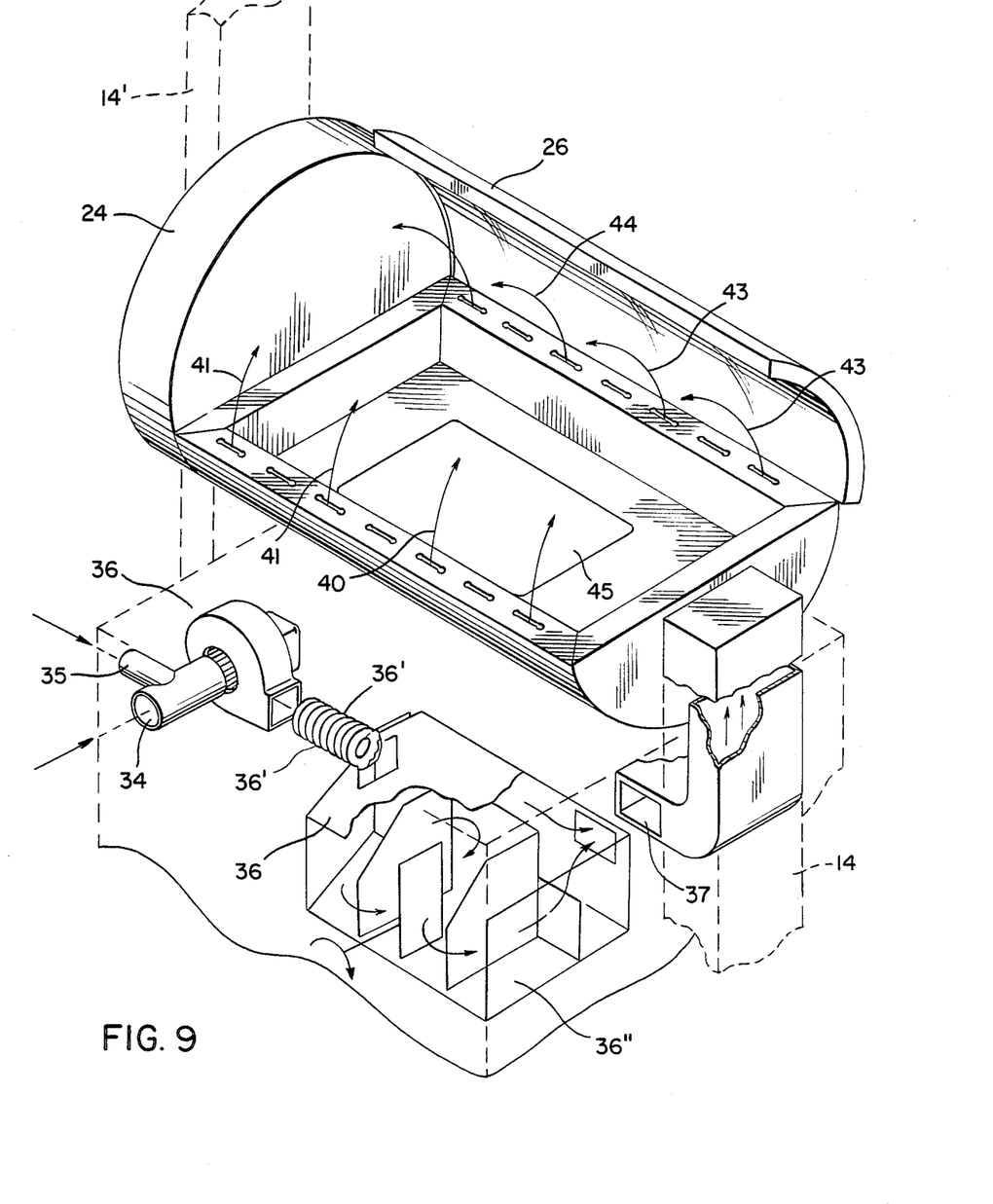

The above is further illustrated with reference to FIG. 8, which shows in a perspective phantom view the operation of the air circulation system: here the air-washing system including 36' the air heater, 36 the blower, the arrows indicating the directions of air flow through the entire system.

There can be advantageously provided sensing means for the more important parameters, such as air temperature, air humidity, skin temperature of the infant, pulse rate of the infant, weight of the infant, etc. There can be provided recording means for the above.

There are advantageously provided alarm means for indicating immediately any deviation from the permitted range of parameters, thus alerting the attendant personnel to take immediate action.

The novel system unifies in a single unit the conventional incubator and an intensive care unit, providing at the same time various additional important improvements which provide for ease of operation and for updated immediate information on the state of the environment of the infant and on its condition (temperature, pulse, rate of breathing, etc.)

The double-walled side windows of equal radius permit ready access from both sides of the incubator at the same time. It further provides for the weighing of the infant in the incubator.

It is clear that the above description is by way of illustration only and that various changes and modifications in the nature and arrangement of parts may be resorted to without departing from the scope and spirit of the Invention.

We claim:

1. An incubator for premature infants and for use as a normal incubator and as an intensive care incubator, said incubator comprising:

a housing defining a cylindrical surface formed by a removable roof-section, two transparent double walled side windows and a lower portion, balancing counterweight means for each of said two windows for maintaining said two windows in any desired position, means for establishing a curtain of air flowing from said lower portion in an upward direction and along the plane of said cylindrical surface of said housing, said means for establishing a curtain of air including means for conditioning the air to a predetermined temperature and humidity, said windows being pivotably mounted around the central axis of said cylindrical surface enabling the windows to move to provide access to the interior of said housing, said windows being set at a desired angle and maintained in position by said counterweight means, said windows being movable around said lower portion, at which position, after the roof has been removed, the incubator serves as an intensive care unit, and illumination means for illuminating said housing from above including means for IR radiation heating.

2. An incubator according to claim 1, wherein said windows are made from two panes of curved plastic joined to form an enclosed air-space between them, each of the windows spanning an angle of from about 45° to about 65°.

3. An incubator according to claim 1, wherein a hinged section in a wall of said housing provides for the pulling out of an infant from within the housing.

4. An incubator according to claim 1, further comprising load cell means for weighing an infant inside the incubator.

5. An incubator according to claim 1, wherein in said illumination means there is also provided means for radiant heating.

* * * * *